United States Patent

Link

[11] Patent Number: 5,197,943
[45] Date of Patent: Mar. 30, 1993

[54] FINGER SPLINT

[75] Inventor: Helmut D. Link, Hamburg, Fed. Rep. of Germany

[73] Assignee: Waldemar Link GmbH & Co., Hamburg, Fed. Rep. of Germany

[21] Appl. No.: 635,113

[22] PCT Filed: May 9, 1990

[86] PCT No.: PCT/EP90/00743
§ 371 Date: Jan. 15, 1991
§ 102(e) Date: Jan. 15, 1991

[87] PCT Pub. No.: WO90/14057
PCT Pub. Date: Nov. 29, 1990

[30] Foreign Application Priority Data

May 19, 1989 [DE] Fed. Rep. of Germany ... 8906213[U]
Dec. 13, 1989 [DE] Fed. Rep. of Germany ... 8914648[U]

[51] Int. Cl.$^5$ .................... A61F 5/00; A41D 45/10
[52] U.S. Cl. ...................... 602/5; 602/22; 2/21
[58] Field of Search .............. 602/21, 22, 30, 20, 602/62, 5; 2/21

[56] References Cited

U.S. PATENT DOCUMENTS

| | | | |
|---|---|---|---|
| 1,375,690 | 4/1921 | George | 602/22 |
| 1,617,942 | 2/1927 | Foulke | 602/22 |
| 1,684,076 | 9/1928 | Smith | 602/22 |
| 1,917,794 | 7/1933 | Brown | 602/22 |
| 2,207,251 | 4/1941 | Longfellow | 602/22 |
| 2,548,378 | 4/1951 | Kleinfold | 602/22 |
| 3,070,091 | 12/1962 | Barnard | 602/22 |
| 3,170,460 | 2/1965 | Stilson | 602/22 |
| 4,644,941 | 2/1987 | Ogle | 602/22 |
| 4,674,487 | 6/1987 | Schaeffer | 602/22 |
| 5,031,608 | 7/1991 | Weinstein | 602/22 |

Primary Examiner—Robert A. Hafer
Assistant Examiner—Michael Brown
Attorney, Agent, or Firm—Chilton, Alix & Van Kirk

[57] ABSTRACT

Finger splint for fixing the distal finger joint in an oblique position, consisting of a shell (1) supporting the distal finger joint and the distal phalanx of the finger on the underside, which are connected to one another near the distal finger joint by means of an annular part (3). In order to be able to permit an adaptation to different swellings of the finger, while at the same time retaining the splint shape adapted anatomically to the finger, the upper-side shell (2) is made divided (longitudinal slot 5) and the splint consists of elastically or plastically flexible material.

18 Claims, 2 Drawing Sheets

FINGER SPLINT

BACKGROUND OF THE INVENTION

This invention relates to a finger splint for fixing the distal finger joint in the extended position, consisting of a shell supporting the distal finger joint and the distal phalanx on the underside, and a shell supporting the distal finger joint and the middle phalanx on the upper side, which shells are connected to one another near the distal finger joint by means of an annular part.

In known finger splints of this type (EP-A 0,183,021), the two shells are in each case made undivided. Therefore, even if they are made of deformable material, they are nevertheless practically unable to yield. This has the disadvantage that the splint cannot resiliently follow, for example, subsiding swellings at the base of the distal phalanx of the finger. In the usual applications of finger splints, for example fractures of the distal phalanx, surgical care of extensor tendon ruptures and inflammation of the nail area, the distal phalanx of the finger is significantly swollen and sensitive, particularly on the dorsal side. This makes it necessary to use correspondingly larger splints which, however, then prove too wide in the area of the middle phalanx of the finger and therefore fit poorly and cannot be fixed correctly. They twist round easily and do not give correct support.

In U.S. Pat. No. 2,528,456 an attempt is made to provide a finger splint with the possibility of adapting to different finger diameters in the different areas of its longitudinal extent by virtue of the fact that it is composed of a plurality of tongues which extend in the circumferential direction and are secured on a common, continuous splint part. The tongues are made elastically resilient so that they can adapt to the thickness of the particular area of the finger surrounded by them, and their ends overlap the continuous splint part. The resilient tongues have the disadvantage that they continuously and unavoidably exert pressure on the finger. This is exactly what it is intended to avoid using the type of finger splint to which the invention relates, namely by using two shells lying on opposite sides of the finger, in different areas thereof, adapted to the shape of the finger and connected rigidly to one another.

EP-A 0,162,692 discloses a finger splint which comprises a resilient annular part, and departing from this and extending in the longitudinal direction, tongues which are held together by means of displaceable rings. Depending on the thickness of the finger, narrower or wider rings can be pushed on, by means of which the tongues extending in the longitudinal direction are held together more tightly or more loosely. In this case, the set spacing of the longitudinal tongues in each case corresponds to the thickest part of the finger, whereas it cannot lie on the thinner areas. The consequence of this is that no correct guiding can be obtained in the thinner areas of the finger.

DE-A 3,026,839 discloses a finger splint of the type to which the invention also relates. It is connected by means of a link to a further splint part which is supported on the proximal phalanx of the finger and is slotted. In contrast, those splint parts supporting the distal phalanx on the underside and the middle phalanx on the upper side are made rigid and undivided in the conventional manner. This document is therefore evidence of the previous medical view that the generic type of finger splint must be rigid per se in order to be able to achieve the desired, anatomically adapted support effect.

SUMMARY OF THE INVENTION

The invention is based on the object of providing a splint of the type mentioned at the outset, which does not have the disadvantages mentioned there.

The solution according to the invention consists in the fact that the upper-side shell is made divided and the splint consists of elastically or plastically flexible material.

The invention adheres to the anatomical adaptation of the splint shape, but makes a break with the received opinion that all parts of this splint must be connected rigidly to one another and in themselves, in order to be able to achieve the anatomically correct support effect; however, this break is only made selectively, namely with respect to the upper shell supporting the middle phalanx. The dimensional stability of the shell supporting the distal phalanx and the distal finger joint on the underside remains unchanged. It has been shown that, despite the anatomical adaptation of the splint shape to the shape of the finger, and with retention of the anatomically correct support effect, it is possible in this way to achieve an adaptation in the rear splint area, which adaptation can lead to proper care in the said cases in which part of the finger is swollen due to inflammation or effusion of blood. This is achieved by virtue of the fact that the splint consisting of elastically or plastically flexible material has the capacity to yield correspondingly. The division is advantageously made continuous. However, the possibility should not be ruled out of the separated shell parts remaining connected to one another in the rear or front area, which contributes to stabilising the splint without reducing its extensibility particularly in the area of the distal phalanx of the finger.

An advantageous embodiment of the invention is distinguished in that, when the finger splint is in the unstressed state, the slot dividing the middle phalanx support becomes wider towards the rear in wedge formation. The advantage of this is that the middle phalanx support can be bent together easily for adaptation to the middle phalanx and/or the middle finger joint, if this is necessary, without thereby creating the risk of a mutual overlapping of the splint parts. Despite the smaller width of the slot in the area of the annular part, such a risk does not generally arise there because the annular part has greater rigidity than the rearwards-projecting parts of the middle phalanx support. Therefore, according to the invention, the annular part can also be divided by the slot. However, in another advantageous embodiment, the annular part is undivided, so that the slot or the slots only in the area of the middle phalanx support divide off from one another several tongues interconnected in the annular part. The advantage of the latter is that pulling together the tongues forming the middle phalanx support does not affect the width of the splint in the area of the distal finger joint, which is useful for example in the case of swelling of this joint.

The tongues forming the middle phalanx support are advantageously of approximately constant width; however, it is also conceivable for them to be slightly narrower towards the rear. When the finger splint is in the unstressed state, the spacing of adjacent tongues is, at least at their rear end, of the order of magnitude of approximately half a tongue's width or even more.

A finger splint has proven advantageous, for example, in which the middle phalanx support is made up of three to five tongues which are of approximately equal width and which together surround slightly more than the upper half of the middle phalanx of the finger.

BRIEF DESCRIPTION OF THE DRAWINGS

The invention is described in greater detail below with reference to the drawing, which illustrates an advantageous exemplary embodiment and in which.

DETAILED DESCRIPTION OF THE INVENTION

Figure 1:
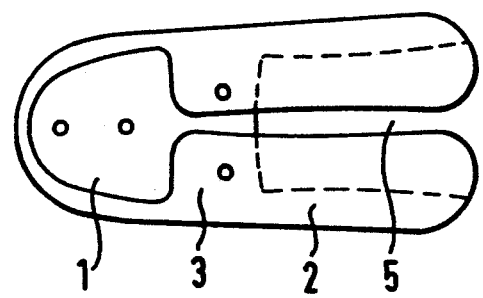
FIG. 1 is a plan view.
Figure 2:
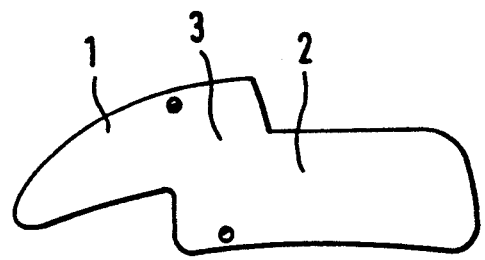
FIG. 2 is a side view.
Figure 3:
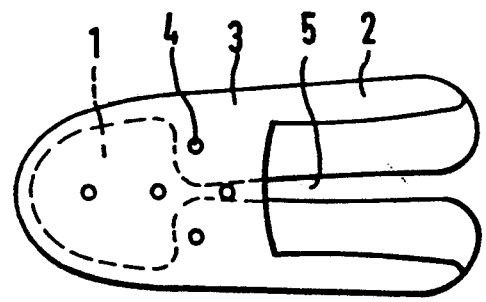
FIG. 3 is a bottom view of a first embodiment of the finger splint.
Figure 6:
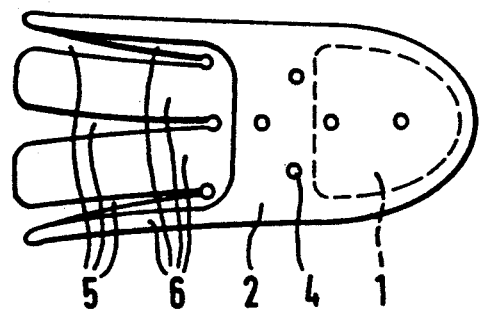
FIGS. 4 to 6 are corresponding views of a second embodiment.
Figure 5:
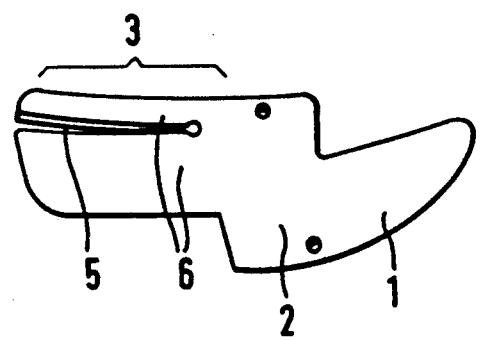

The finger splint consists of the shell 1 supporting the distal phalanx of the finger and the distal finger joint on the underside, the shell 2 supporting the middle phalanx of the finger and the distal finger joint on the upper side, and the lateral transition area 3 connecting the two shells on both sides integrally and firmly with one another, which transition area 3 combines with the rear part of the shell 1 and the front part of the shell 2 to form an annular section. The shell 1 can have an oval cutout on the underside. The shell 2 can have a larger cutout on the upper side. This is known per se. Ventilation openings 4 are indicated in the drawing.

In the middle in the longitudinal direction the shell 2 is divided by a slot 5 into two identical shell halves. In the view shown, in which the finger splint presents its normal width, the slot 5 has a width of 0 to 5, preferably 1 to 3 mm, so that it permits not only a widening of the splint, but also a certain peripheral contraction.

In the example shown, the slot 5 is made straight in the longitudinal direction of the splint. However, it can also be made at an angle, curved, undulating or serrated, for example.

In the second embodiment, the middle phalanx support 3 is divided by means of three slots 5 into four tongues 6 of approximately equal width. Because the tongues 6 are connected firmly to one another at their front end by means of the annular part 2, they cannot significantly converge upon one another there, even if they are applied to a comparatively thin middle phalanx of the finger. They cannot therefore exert any undesired pressure there. The situation is different at the rear end, where the relative convergence can be significantly greater. For this reason, the slots 5 are designed widening rearwards in wedge formation.

The finger splint is made of comparatively easily deformable material, such as polyethylene, with a thickness of between 1 and 1.5 mm. By virtue of their mutual separation, the tongues forming the support part 3 are easily deformable. Nevertheless, they surprisingly complement one another to give the necessary splint rigidity, because each conceivable bending moment, which could be transferred to the splint in the area of the support part, runs in the direction of the greater moment of resistance of at least one of the tongues. The pliability of the tongues about bending axes running parallel to their thin transverse direction therefore make the support part capable of adaptation, without reducing its rigidity necessary for the splint to function. If only bending moments are to be absorbed in a certain preferred direction, it is possible to do without those tongues which do not afford any substantial rigidity in this direction. For example, if the support is to act only against bending moments acting around axes parallel to the joint axes, the two middle tongues can be omitted, for example.

Figure 4:
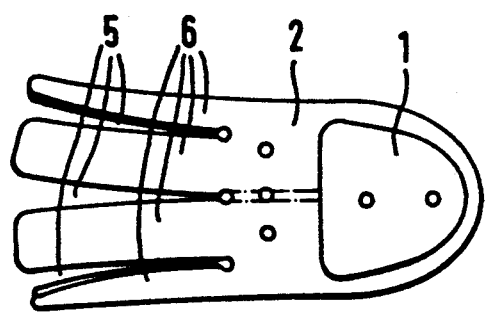

The broken lines in FIG. 4 indicate the course of the middle slot 5 when the latter not only cuts through the middle phalanx support 3, but also the annular part 2.

I claim:

1. Finger splint for fixing a distal finger joint in an extended position, the splint having a length, the distal finger joint joining a distal phalanx and a middle phalanx, each of the distal finger joint, distal phalanx, middle phalanx and finger splint having an upper side and an under side, the upper side and under side being generally opposite each other in a direction which is perpendicular to the length of the splint, the splint comprising a first shell on the under side thereof for supporting the distal finger joint and the distal phalanx on the under side and a second shell on the upper side of the finger splint for supporting the distal finger joint and the middle phalanx on the upper side, the first and second shells being connected to one another near the distal finger joint by means of an annular part, wherein the second shell includes an opening on the under side of the finger splint and has a substantially longitudinal slot on the upper side of the finger splint, and wherein the splint consists essentially of at least one of elastically and plastically flexible material.

2. Finger splint according to claim 1, wherein the slot is continuous.

3. Finger splint according to claim 1, wherein, when the finger splint is in an unstressed state, the slot becomes wider in a direction away from the first shell in a wedge formation.

4. Finger splint according to claim 3, wherein the second shell is made up of several tongues interconnected in the annular part, the tongues being separated from one another by slots.

5. Finger splint according to claim 4, wherein, when the finger splint is in an unstressed state, the slots separating the tongues from one another widen in a direction away from the first shell.

6. Finger splint according to claim 4, wherein the tongues are of approximately constant width.

7. Finger splint according to claim 6, wherein, each tongue has a first end proximate the annular part and a second opposite end, and when the finger splint is in the unstressed state, adjacent tongues have a spacing, at the second end, of approximately half a tongue's width or more.

8. Finger splint according to claim 4, wherein the second shell is made up of three to five tongues of approximately equal width.

9. Finger splint according to claim 1, wherein the annular part is undivided.

10. Finger splint for fixing a distal finger joint in an extended position, the splint consisting essentially of elastically or plastically flexible material and comprising a distal phalanx support, a middle phalanx support, and an annular part connecting the distal phalanx support and middle phalanx support, each of the distal phalanx support, middle phalanx support and annular part having an under side adjacent the bending direction of the distal finger joint and an upper side opposite to the respective under side in a direction substantially perpendicular to the direction from the distal phalanx support to the middle phalanx support, the distal phalanx support comprising a first shell which is substantially closed on the under side and is substantially open on the upper side, and the middle phalanx support comprising a second shell which is substantially open on the under side, is substantially closed on the upper side, and has a longitudinal slot formed on the upper side.

11. A finger splint according to claim 10, wherein the slot is continuous.

12. A finger splint according to claim 11, wherein the annular part is undivided.

13. A finger splint according to claim 10, wherein, when the finger splint is in an unstressed state, the slot widens in a direction away from the distal phalanx support in a wedge formation.

14. A finger splint according to claim 13, wherein the middle phalanx support includes several tongues which are connected to the annular part, the tongues being separated from each other by additional slots.

15. A finger splint according to claim 14, wherein, when the finger splint is in an unstressed state, the additional slots widen in a direction away from the distal phalanx support.

16. A finger splint according to claim 14, wherein the tongues have approximately constant widths.

17. A finger splint according to claim 16, wherein each tongue has a first end connected to the annular part and an opposite second end, and when the finger splint is in an unstressed state, adjacent tongues have a spacing of approximately one half of a tongue's width or more at the second end.

18. A finger splint according to claim 14, wherein the middle phalanx support is formed from three to five tongues of approximately equal width.

* * * * *